(12) United States Patent
Malkar et al.

(10) Patent No.: US 7,572,832 B2
(45) Date of Patent: Aug. 11, 2009

(54) NON-HYGROSCOPIC L-CARNITINE SALTS

(75) Inventors: Navdeep B. Malkar, Cary, NC (US); Deanna J. Nelson, Raleigh, NC (US)

(73) Assignee: Biolink Life Sciences, Inc., Cary, NC (US)

( * ) Notice: Subject to any disclaimer, the term of this patent is extended or adjusted under 35 U.S.C. 154(b) by 0 days.

(21) Appl. No.: 11/725,365

(22) Filed: Mar. 19, 2007

(65) Prior Publication Data
US 2008/0234371 A1   Sep. 25, 2008

(51) Int. Cl.
*A61K 31/205* (2006.01)
*C07C 229/00* (2006.01)

(52) U.S. Cl. ........................................ 514/556; 562/567
(58) Field of Classification Search ................... None
See application file for complete search history.

(56) References Cited

FOREIGN PATENT DOCUMENTS
GB             2052976 A   *   2/1981

* cited by examiner

*Primary Examiner*—Paul A Zucker
(74) *Attorney, Agent, or Firm*—Casimir Jones, S.C.

(57) ABSTRACT

Stable and non-hygroscopic L-carnitine salts of organic acids are provided, each of which is present as a true complex salt, having the formula:

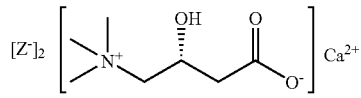

wherein Z is acetate, propionate, or butyrate. In addition, processes for the preparation of these compounds are provided, together with the use of these compounds as a source of both L-carnitine and the calcium ion in nutrition or as a pharmaceutical active ingredient having therapeutic pharmacological activity.

6 Claims, 3 Drawing Sheets

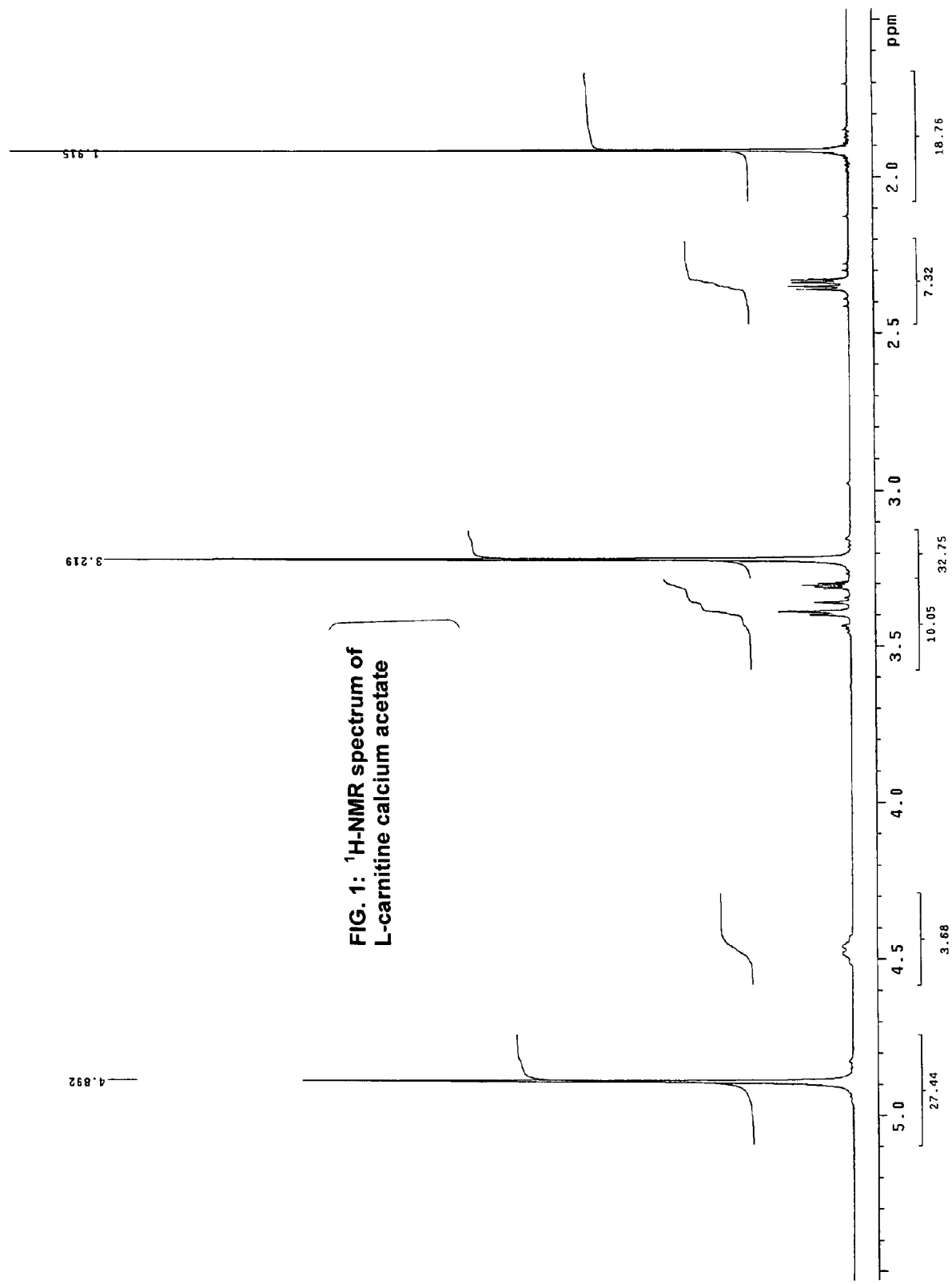
FIG. 1: ¹H-NMR spectrum of L-carnitine calcium acetate

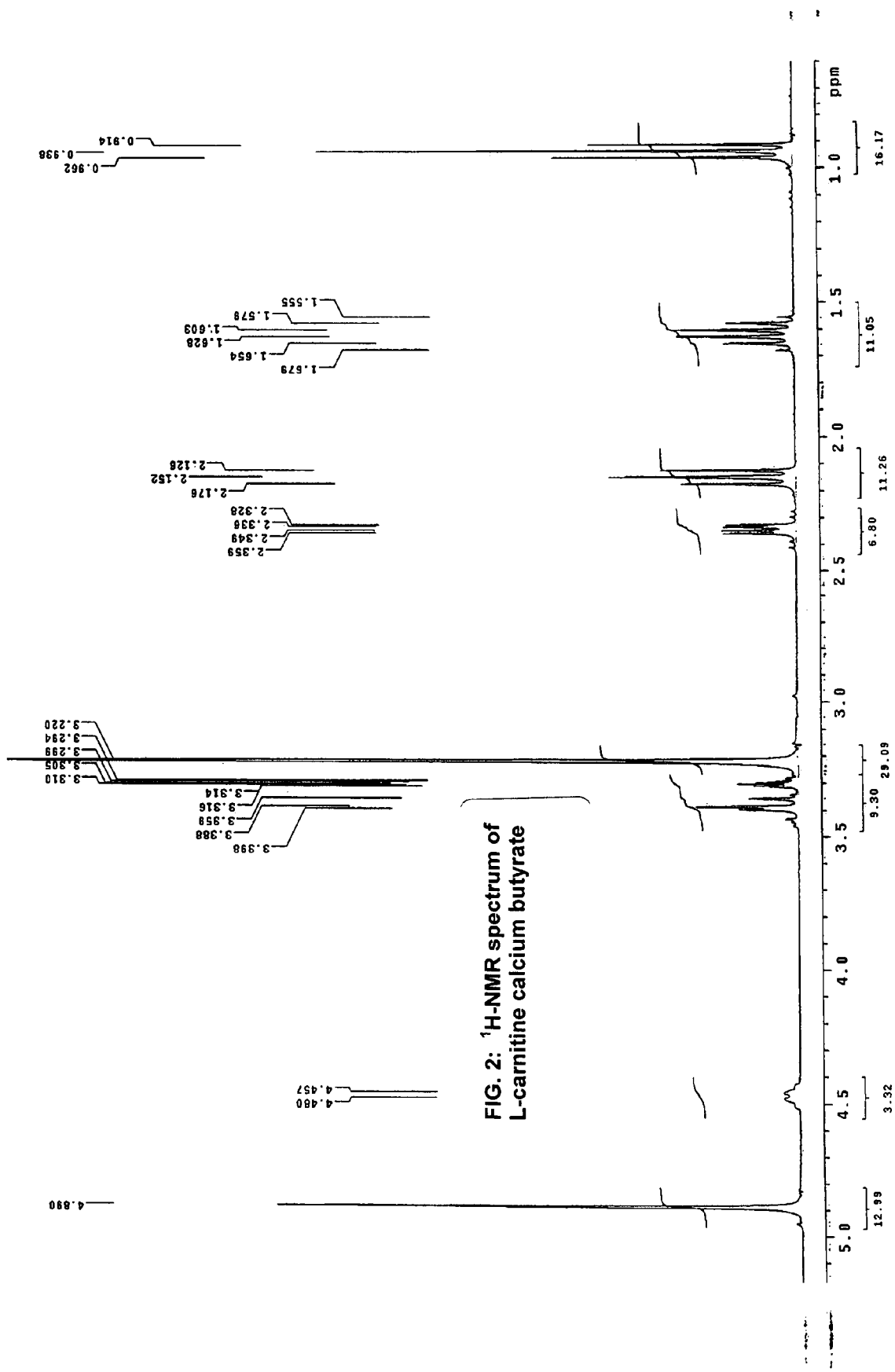
FIG. 2: ¹H-NMR spectrum of L-carnitine calcium butyrate

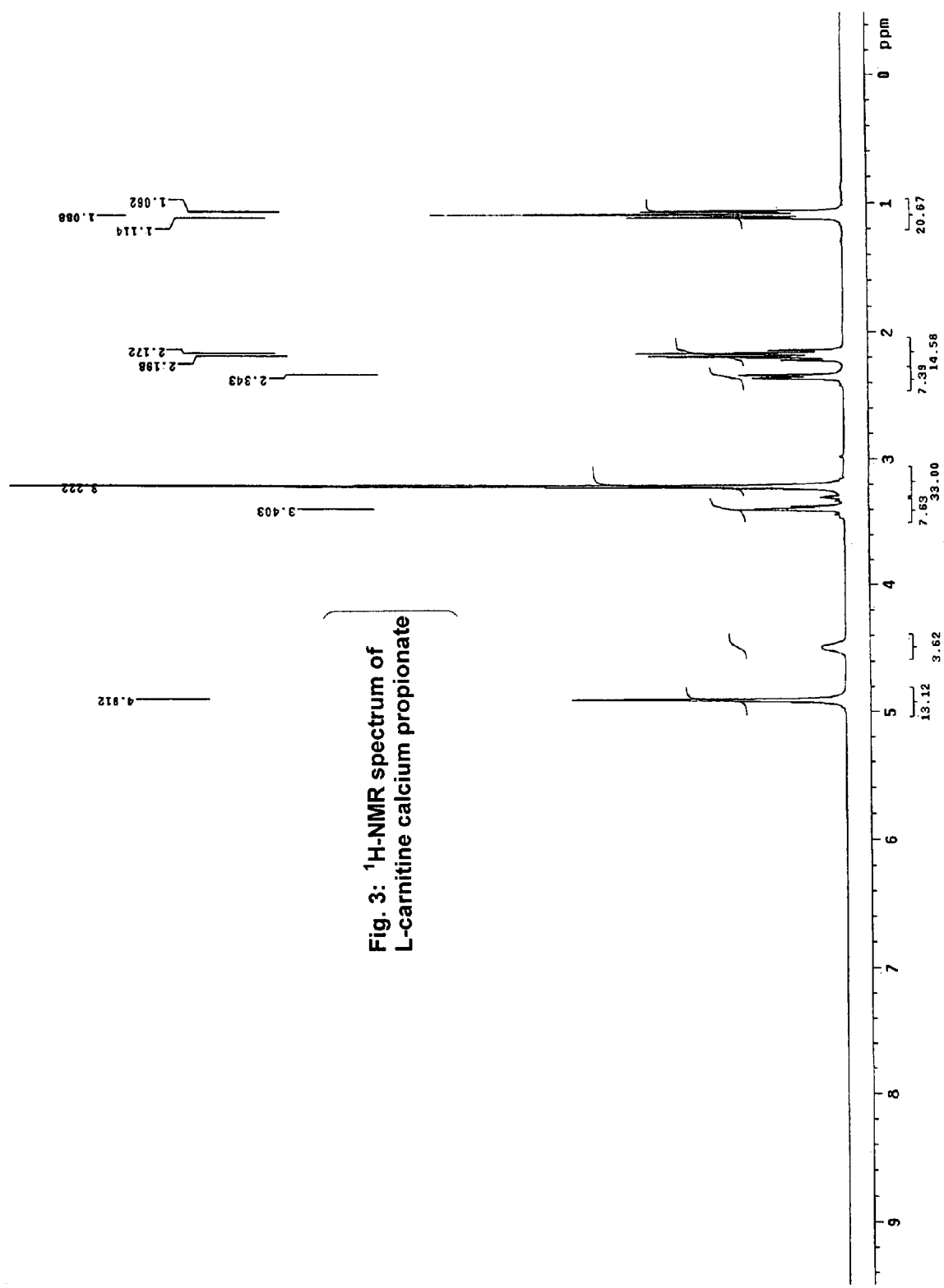

NON-HYGROSCOPIC L-CARNITINE SALTS

BACKGROUND OF THE INVENTION

L-(−)-Carnitine is a vitamin-like nutrient that is essential for energy production and fat metabolism in the physiological systems of birds, fish, and mammals. L-Carnitine has the molecular formula:

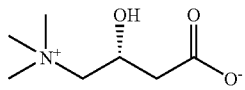

L-carnitine is supplied to the body through both endogenous synthesis (about 25% of the adult daily requirement) and food intake (about 75% of the adult daily requirement). The main dietary source of L-carnitine is meat; beef and lamb provide the most dietary L-carnitine. (Fruits and vegetables provide only traces of L-carnitine.) Within the human body, the major sites of L-carnitine biosynthesis are the liver and kidney, as well as the brain and testes. Biosynthesis requires lysine, methionine, vitamin C, iron, vitamin $B_6$, and niacin.

L-(−)-Carnitine functions as a requisite mediator of acyl transport and accepts acyl groups from a variety of acylCoA derivatives in cells and tissues throughout the body. In humans, the transport activity of L-carnitine is particularly important in working muscle, for example, in the skeletal muscles and the heart. Both types of tissues are dependent on fatty acid metabolism for energy supply, and L-carnitine mediates the translocation of fatty acyl groups across mitochondrial membranes to the sites of oxidation in the mitochondria. In addition, L-carnitine shuttles short chain fatty acids from inside the mitochondria to the cytosol. Other physiological roles of L-carnitine include mitochondrial long-chain fatty acid oxidation, buffering of the mitochondrial acyl CoA/CoA couple, scavenging acyl groups, peroxysomal fatty acid oxidation, branched-chain amino acid oxidation, and membrane stabilization.

An incomplete diet, physiological stress situations, such as exercise or pregnancy, and metabolic dysfunction, in particular, lipid disorders or diseases of the liver and kidney, create a need for L-carnitine supplementation. In addition, L-carnitine is an essential nutrient for infants, since neonates and young children lack the capacity to synthesize L-carnitine in the quantities that are needed for optimal development.

Because L-carnitine functions as a requisite mediator of acyl transport in the body, an L-carnitine deficiency is a serious physiological disorder. Individuals who suffer from L-carnitine deficiency are afflicted with muscle weakness (myasthenia), accompanied by an accumulation of lipids in specific types of muscle fibers. Severe L-carnitine deficiency may present as myasthenia gravis. Individuals who suffer from systemic L-carnitine deficiency and also secondary L-carnitine deficiency associated with organic acidemias may experience vomiting, stupor, confusion and in severe or prolonged occasions of systemic L-carnitine deficiency accompanied by stressful stimuli, coma in encephalopathic episodes.

It is known that L-carnitine is very hygroscopic. The hygroscopicity of L-carnitine causes a lack of storability of the solid substance and of simple powder mixtures prepared therefrom, and causes problems such as inadequate flowability during further formulating, processing, and manufacturing of orally administrable dosage forms of pure solid L-carnitine or powdered mixtures containing L-carnitine for use in food, nutritional or dietary supplements for humans or other mammals, animal feed or dietary supplements, or drugs for human or veterinary use. However, oral dosage forms represent the preferred dosage forms, inasmuch as they make it particularly easy for users to take the active ingredient and comply with optimal dosage regimens.

Further, it is known that L-carnitine exhibits a distinctly objectionable malodor and a distinctly distasteful taste after ingestion. The noxious odor and taste render ingestion of oral dosage forms of L-carnitine difficult and interfere with compliance to optimal dosage regimens. Thus, there is a significant unmet need for a form of L-carnitine that is free from noxious odor or taste.

Calcium ($Ca^{2+}$) is the major extracellular divalent cation. $Ca^{2+}$ is essential for bone development and maintenance and functions in many other important physiological processes, including neuronal excitability, neurotransmitter release, muscle contraction, membrane integrity, and blood coagulation. In addition, $Ca^{2+}$ serves a second messenger function for the actions of many hormones.

Exogenous $Ca^{2+}$ is conventionally supplied by ingestion of oral compositions containing calcium salts. Among the conventionally used calcium salts are calcium carbonate, calcium acetate, calcium gluconate, calcium citrate, calcium chloride, and calcium phosphate. Many of the conventional calcium salts have objectionable tastes; ingestion of calcium acetate, for example, causes regurgitation of acetic acid and "vinegar breath." Other conventional calcium salts, such as calcium carbonate, for example, are "chalky" and have widely variable bioavailability through absorption from the gastrointestinal tract. Further, calcium carbonate that is prepared from limestone contains traces of toxic metals such as lead and aluminum. Thus, there is a significant unmet need for a $Ca^{2+}$ salt that is free from noxious taste, objectionable after-effects of ingestion, and toxins.

There is now an extensive body of literature, including patents, disclosing the production of allegedly stable, non-hygroscopic L-carnitine salts (Table 1).

TABLE 1

Conventional L-Carnitine Salts that are manufactured at commercial scales and available commercially

| L-Carnitine Salt | Drawback |
|---|---|
| L-Carnitine acid fumarate (U.S. Pat. No. 4,602,039, Sigma-Tau) | Not a source for both L-carnitine and calcium. |
| L-carnitine L-(+)-tartrate (U.S. Pat. No. 5,703,376, Lonza) | Not a source for both L-carnitine and calcium. Not a physiological organic acid. |

TABLE 1-continued

Conventional L-Carnitine Salts that are manufactured at commercial
scales and available commercially

| L-Carnitine Salt | Drawback |
| --- | --- |
| Acetyl L-carnitine galactarate (U.S. Pat. No. 5,952,379, Sigma-Tau) | Not a source for both L-carnitine and calcium. Galactarate is the anion of an unnatural polyhydroxy polybasic acid (i.e., it is not a substance found in physiological systems). |
| L-carnitine magnesium citrate (U.S. Pat. No. 5,071,874, Lonza) | Not a source for both L-carnitine and calcium. |
| L-Carnitine calcium galactarate and L-carnitine magnesium galactarate (Fassi, WO 02/059075 A1) | Not yet commercially available. Galactaric acid is an unnatural polyhydroxy polybasic acid (i.e., it is not a substance found in physiological systems). |

When used as a dietary supplement and exogenous source of L-carnitine, gram quantities of conventional L-carnitine compounds may be ingested each day for extended periods of time. Likewise, gram quantities of calcium compounds may be ingested daily to provide exogenous calcium as a dietary supplement to promote bone development and prevent osteoporosis, for example. Women and children conventionally use both L-carnitine and calcium supplements having these dosage regimens. The chronic dosage amounts thus utilized are sufficiently sizeable that it is important to provide L-carnitine calcium compositions in which all components are either metabolized to innocuous products or do not accumulate and potentially cause toxicity.

The important physiological roles played by $Ca^{2+}$ and L-carnitine and the various pathological disturbances or states induced by serious deficiencies of these substances have been known for decades.

Therefore, there is a significant unmet need for stable, non-hygroscopic sources of L-carnitine and calcium in order to allow the preparation of orally or intravenously administrable compositions to be used as sources of L-carnitine and calcium in all those situations wherein calcium and/or L-carnitine supplementation prevents the onset or reverses the course of deleterious effects brought about by their deficiency. The present invention addresses this significant unmet need.

SUMMARY OF THE INVENTION

The invention relates to non-hygroscopic L-carnitine salts, including L-carnitine calcium salts of organic acids, each of which is present as a true complex salt, to a process for the preparation of these compounds, and to the use of these compounds as a source of both L-carnitine and the calcium ion in nutrition or as a pharmaceutical and pharmacologically active ingredient. A compound of the present invention has the following formula:

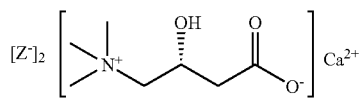

wherein Z is acetate, propionate, or butyrate. The invention also provides a method for preparing L-carnitine calcium compounds of the present invention, comprising reacting L-carnitine, calcium ion, and an anion of an organic acid in a 1:1:2 molar ratio in a suitable solvent and obtaining the product of said reaction. Further, the invention provides a method for preventing the onset or reversing the course of deleterious effects brought about by L-carnitine or calcium deficiency comprising administering an L-carnitine salt composition of the present invention.

BRIEF DESCRIPTION OF THE DRAWINGS

FIG. 1 is the $^1$H-Nuclear Magnetic Resonance ($^1$H-NMR) spectrum of L-carnitine calcium acetate in perdeuteromethanol.

FIG. 2 is the $^1$H-NMR spectrum of L-carnitine calcium butyrate in perdeuteromethanol.

FIG. 3 is the $^1$H-NMR spectrum of L-carnitine calcium propionate in perdeuteromethanol.

DETAILED DESCRIPTION OF THE INVENTION

The main object of the invention is to provide a new derivative of L-carnitine which exhibits an absence of hygroscopicity and good thermal stability. Other objects and advantages of the invention are set out herein or are obvious herefrom to one skilled in the art. The objects and advantages of the invention are achieved by the compounds and processes of the invention.

The invention comprises stable, non-hygroscopic L-carnitine salts of calcium and an organic acid having the formula (I):

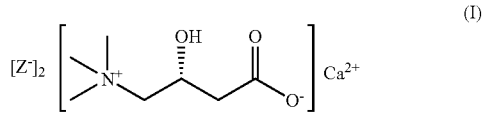

wherein Z is acetate, propionate, or butyrate.

The invention also involves a process for the production of L-carnitine salts having formula (I).

Further, the invention involves the use of L-carnitine salts having formula (I) as a food additive, nutritional supplement, dietary supplement, medical food, nutrient, and source of L-carnitine and/or calcium in the field of nutrition for humans, animals, fish, and birds. The invention further involves the use of L-carnitine salts having formula (I) as a pharmaceutical and pharmacologically active ingredient for human clinical and veterinary applications.

The invention further comprises a method of administering an L-carnitine salt having formula (I) to a subject in need of such administration for the prevention or treatment of L-carnitine and/or calcium deficiency.

According to the method of the present invention, an L-carnitine salt having formula (I) is administered, alone or in combination with other substances (e.g., along with materials necessary to form a tablet, caplet, pill, capsule, troche, lozenge, powder, granulate, or solution that is suitable for ingestion) in sufficient quantities to prevent the onset or reverse the course of deleterious effects brought about by L-carnitine and/or calcium deficiency. Further, according to the method of the present invention, an L-carnitine salt having formula (I) is administered, alone or in combination with other substances, in sufficient quantities in a formulation for parenteral administration to prevent the onset or reverse the course of deleterious effects brought about by L-carnitine and/or calcium deficiency.

In the method of the present invention, a composition as described hereinabove is administered to a mammal by oral ingestion or injection. The composition, so administered, may be regarded either as a food additive, a substance that is generally regarded as safe (i.e., a GRAS substance), or a drug within the meaning of Title 21 of the Code of Federal Regulations (CFR).

In the method of the present invention, a composition as described hereinabove may be ingested as a food supplement, dietary supplement, nutritive supplement, or medical food. By the terms "food supplement, dietary supplement, and nutritive supplement" is meant that a composition of the present invention exogenously augments the L-carnitine and/or calcium that is present in food, components of the diet, and compositions intended to provide nutrition. By the term "medical food" is meant that a composition of the present invention is prescribed by a clinician for the purpose of exogenously augmenting L-carnitine and/or calcium in ingesta.

In the method of the invention, a composition as described hereinabove may be administered as a drug either orally or by injection.

Included within the scope of this invention is a method of treating calcium and/or L-carnitine deficits in a warm-blooded animal using pharmaceutical compositions comprising L-carnitine salts having formula (I) and a suitable pharmaceutical carrier. For the purpose of this disclosure, a warm-blooded animal is a member of the animal kingdom which includes but is not limited to mammals and birds. The most preferred mammal of this invention is human.

The term "Ca" means the calcium ion $Ca^{2+}$.

The term "non-hygroscopic" means the ability endowed by certain L-carnitine salts, when they occur as powders or granules, to withstand exposure to the water vapor of an ambient atmosphere for 24 hours or longer without giving rise to adverse phenomena of aggregating, agglomerating, absorbing water, or deliquescing which results in loss of their flowability.

The term "true complex salt" as used herein generally means a salt comprising a metal cation and associated anions, each present in sufficient number to provide charge balance. A true complex salt has a composition, a molecular weight, and other physico-chemical properties such as melting point that are characteristic of the salt.

The term "excipient material" means any compound forming a part of the formulation which is not intended to have biological activity itself and which is added to a formulation to provide specific characteristics to the dosage form, including by way of example, providing protection to the active ingredient from chemical degradation, facilitating release of a tablet or caplet from equipment in which it is formed, and so forth.

The terms "treating" and "treatment" and the like are used herein to generally mean obtaining a desired pharmacological and physiological effect. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment" as used herein encompasses any treatment of a disease in a mammal, particularly a human and includes: (a) preventing the disease from occurring in a subject which may be predisposed to the disease but has not yet been diagnosed as having it; (b) inhibiting the disease or arresting its development; (c) relieving the disease, causing regression of the disease and/or its symptoms or conditions; or (d) returning a clinical value to the concentration range normally found in a subject.

The phrase "therapeutically effective" is intended to qualify the amount of L-carnitine salts having formula (I) for use in an orally or intravenously administered therapy which will achieve the goal of abating, mitigating, reducing or preventing, for example, a calcium and/or L-carnitine deficiency disorder, or of restoring physiologically adequate concentrations of L-carnitine and/or calcium while avoiding adverse side effects typically associated with conventional L-carnitine and/or calcium compositions.

The terms "sterile" and "sterilized" as used herein have their conventional meanings as understood by skilled artisans when referring to the sterility required pharmaceutically for intravenous preparations. Sterilization is achieved conventionally, either by application of heat (e.g., high-pressure steam sterilization or high-temperature short time steam sterilization) or through the use of filters having a pore-size sufficiently small to exclude pathogens.

The term "suitable for intravenous injection" as used herein has its conventional meaning as understood by skilled artisans when referring to a composition that meets the general requirements for solutions for injection as presented in the General Chapter of the U.S. Pharmacopoeia entitled "Injections." (U.S. Pharmacopoeia, U.S. Pharmacopoeial Convention, Inc., Rockville, Md., 2006.)

The term "parenteral nutrition composition" means a hyperalimentation composition for intravenous administration comprising one or more components selected from the group consisting of a carbohydrate solution, an amino acids solution, and lipids.

By the term "physico-chemically compatible" with respect to a component of a parenteral nutrition composition is meant that a disruption of the composition is not observed, as determined by the observation of phase separation, creaming, particulate formation, an increase in the percentage of lipid globules having a diameter greater than 5 μm as measured by conventional light scattering, light obscuration, or particle-sizing techniques, or the like.

The term "dialysis therapy" means the clinical treatment of chronic kidney disease comprising the osmotic exchange of metabolites, toxins and water across a membrane from a renal disease patient's blood to a dialysate solution. Conventional dialysis therapy is described by S. Pastan and J. Bailey in the article entitled "Dialysis therapy" published in The New England Journal of Medicine, volume 338, number 20, pages 1428-1437 (1998).

The term "dialysate" means a composition for intravenous administration as part of a dialysis procedure for the treatment of chronic kidney disease. Dialysate is conventionally provided for use in either peritoneal dialysis (in which the peritoneal membrane constitutes the dialysis membrane) or hemodialysis (in which a synthetic membrane constitutes the dialysis membrane). Hemodialysate is generally prepared from two dry powder concentrates, the A and B concentrates, which are reconstituted in treated water before use, or from two aqueous solutions of the A and B dry powder concentrates. The A concentrate, containing an organic acid and the necessary electrolytes and osmotic agents other than bicarbonate, is mixed with B concentrate containing bicarbonate and treated water in a dialysis machine to make the final hemodialysate. Peritoneal dialysate is a premixed solution of osmotic agents, necessary electrolytes, and water that is used in dialysis without further constitution.

It is understood that any and all whole or partial integers between any ranges set forth herein are included herein.

After lengthy experimentation we have unexpectedly discovered unique, stable, non-hygroscopic L-carnitine salts of organic acids and processes for their preparation. The L-carnitine salts of the present invention are stable, non-hygroscopic salts having formula (I):

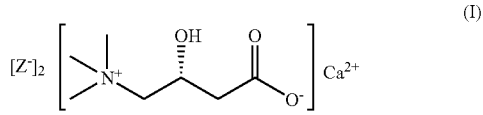

wherein Z is acetate, propionate, or butyrate.

It is surprising that L-carnitine salts having formula (I) are stable and non-hygroscopic. This combination of physicochemical properties is not inherent to L-carnitine salts. During our investigations, we discovered that certain L-carnitine salt compositions lack these advantageous properties. For example, we discovered that compositions comprising L-carnitine and calcium are hygroscopic. Similarly, we discovered that compositions comprising L-carnitine, calcium, and an organic diacid or polyacid in a molar ratio of 1:1:1 were hygroscopic and/or retained an objectionable odor and/or taste. By way of example, compositions comprising L-carnitine, calcium, and fumarate in a molar ratio of 1:1:1 are solids with objectionable odor and taste. Likewise, both L-carnitine calcium succinate and L-carnitine calcium fumarate in molar ratios of 1:1:1 are hygroscopic.

In contrast, we discovered that an L-carnitine salt composition of the present invention having a molar ratio of L-carnitine, calcium, and an anion of an organic acid of 1:1:2 is advantageously stable and non-hygroscopic if the organic acid is acetic acid. In addition, we discovered that an L-carnitine salt composition having formula (I) wherein Z is propionate or butyrate is stable and non-hygroscopic provided that the relative humidity is less than about 20%.

While not wishing to be bound by any particular hypothesis or theory, the inventors expect that the L-carnitine salts of organic acids of the present invention afford the significant advantage that each salt of an organic acid is a physiologically utilized salt. Citrate, isocitrate, acetate, succinate, malate, pyruvate, and lactate are all enzyme substrates in the physiological tricarboxylic acid cycle. Butyrate is an enzyme substrate for endothelial cells in the intestine. Propionate is metabolized via the tricarboxylic acid cycle in a manner that is expected to buttress L-carnitine's utility for effecting weight loss. Therefore, the inventors expect that the L-carnitine calcium salts of organic acids of the present invention will exhibit advantageous biocompatibility as compared to L-carnitine metal salts of organic acids wherein the organic acid is not a physiological substrate or natural substance. Biocompatibility of the L-carnitine calcium salts of the present invention is a particularly advantageous characteristic, in that conventional L-carnitine compounds and calcium salts are typically ingested in gram quantities each day. Women and children, for example, often require L-carnitine or calcium supplementation administered in accordance with this dosage regimen. Biocompatibility of the L-carnitine calcium salts of the present invention ensures that each of the components of the L-carnitine calcium salt of the present invention will be metabolized and will not accumulate, potentially causing toxicity.

The process for the production of L-carnitine calcium salt of an organic acid of the present invention can be performed according to the invention from stoichiometric portions of L-carnitine, a calcium compound, and acetic, propionic, or butyric acid in a molar ratio of 1:1:2 in a suitable solvent, such as water, methanol, ethanol, or combinations thereof. Calcium hydroxide, calcium oxide, calcium carbonate, and calcium chloride can be used as the calcium compound. Preferably the reaction is performed in an aqueous medium. The reaction temperature is suitably 20° to the boiling point of the solvent, preferably about 20° C.

More preferably, the process for the production of L-carnitine calcium acetate or propionate is performed using stoichiometric portions of calcium acetate or calcium propionate and L-carnitine in a suitable solvent, such as water, methanol, ethanol, or combinations thereof. Preferably the reaction is performed in an aqueous medium, where the volume used is the minimum needed to dissolve the reactants. The reaction temperature is suitably 20° to the boiling point of the solvent, preferably 20° C.

According to a preferred variation of the process according to the present invention, an L-carnitine calcium salt of the present invention can be recovered from a solution of calcium ion, acetate, propionate, or butyrate, and L-carnitine by concentration and precipitation. Thus, L-carnitine calcium acetate, L-carnitine calcium propionate, or L-carnitine calcium butyrate is recovered from the solution if the solvent, after a certain reaction time, is then removed by spray-drying, vacuum-drying, freeze-drying, concentrating by evaporation, or the salt is precipitated by addition of an organic solvent. Preferably, the solution is concentrated by evaporation at reduced atmospheric pressure at temperatures of less than about 70° C. or by spray drying. By spray drying, the desired product is obtained in the desired grain size. Instead of spray drying, the solution can be concentrated by evaporation at reduced atmospheric pressure (for example, by evaporation at reduced pressure on a rotary evaporator) at temperatures of less than about 70° C., and the resultant solid residue further treated by a purification treatment/scheme in a suitable solvent.

The methods for the preparation of L-carnitine calcium salts of formula (I) that are disclosed herein are advantageously useful in pharmaceutical manufacturing of these L-carnitine salts, as illustrated by way of example, by the following. The raw materials and solvents are commercially available. Advantageously, from an industrial perspective, the process for the preparation of the aforesaid solid compositions involves the use of conventional apparati and avoids the requirement for dehumidified facilities. The reaction conditions enable control of reaction temperature, monitoring of the progress of reaction for extent of completion, methods for the removal of impurities, and convenient and steps for the recovery of L-carnitine calcium salt of formula (I) from the solution in nearly quantitative yield.

The L-carnitine calcium salts of formula (I) obtained by the methods of the present invention exhibit both high purity and absence of both solvents and chemical and biological contaminants, qualities qualifying L-carnitine calcium salts of formula (I) for use in pharmaceutical formulations. By way of example, L-carnitine calcium acetate of the present invention is a white solid that is not hygroscopic or deliquescent and is stable during storage. L-Carnitine calcium propionate or L-carnitine calcium butyrate of the present invention is a white solid that is not hygroscopic or deliquescent and is stable during storage, provided that the relative humidity is less than about 20%. By way of further example, each of the exemplary L-carnitine calcium salts of the present invention is easily milled or processed into formulary dosage forms using conventional methods and techniques.

The inventors have discovered that simple admixture or combination of L-carnitine and a calcium salt of an organic acid in the absence of a suitable solvent is not sufficient to provide an L-carnitine calcium salt of the present invention. After simple admixture or combination, L-carnitine retains its objectionable malodor and offensive taste, as well as its hygroscopicity, and the calcium salt retains its objectionable organoleptic properties and side effects. Likewise, the inventors have discovered that simple admixture or combination of L-carnitine, an organic acid, and a calcium salt in the absence of a suitable solvent is not sufficient to provide an L-carnitine calcium salt of formula (I). In contrast, use of the methods of preparing the L-carnitine calcium salt of an organic acid of the present invention as disclosed herein provides a stable, non-hygroscopic composition of the present invention.

Further, an L-carnitine calcium salt of an organic acid of the present invention has different physico-chemical properties from the starting materials. As we discovered and disclose in Example 5, for example, L-carnitine calcium acetate, an embodiment of the present invention, has a melting point of 166-167° C., different from the melting point of L-carnitine (186-190° C.) or calcium acetate (does not melt at less than 300° C.). The NMR spectrum of L-carnitine calcium acetate (FIG. 1) confirms the presence of the composition and the 1:2 molar ratio of L-carnitine and acetate. (Calcium is not detected by NMR.) L-carnitine calcium acetate is soluble in water, and aqueous solutions of this salt provide bioavailable L-carnitine, calcium, and acetate.

As we discovered and disclose in Example 6, L-carnitine calcium butyrate, another embodiment of the present invention, is a white solid having a melting point of 97.6° C., different from the melting point of L-carnitine. Butyric acid, a starting material for the preparation of L-carnitine calcium butyrate, is a liquid having a stench; in contrast, L-carnitine calcium butyrate is odorless; ingestion leaves a somewhat bitter after-taste. The NMR spectrum of L-carnitine calcium butyrate (FIG. 2) confirms the presence of the composition and the 1:2 molar ratio of L-carnitine and butyrate. (Calcium is not detected by NMR.) L-Carnitine calcium butyrate is soluble in water, and aqueous solutions of this salt provide bioavailable L-carnitine, calcium, and butyrate.

As we discovered and disclose in Example 7, L-carnitine calcium propionate, an embodiment of the present invention, has a melting point of 166.3° C., different from the melting point of L-carnitine (186-190° C.) or calcium propionate (does not melt at less than 300° C.). The NMR spectrum of L-carnitine calcium propionate (FIG. 3) confirms the presence of the composition and the 1:2 molar ratio of L-carnitine and propionate. (Calcium is not detected by NMR.) L-carnitine calcium propionate is soluble in water, and aqueous solutions of this salt provide bioavailable L-carnitine, calcium, and propionate.

The compounds of the invention provide an ideal ratio of L-carnitine and calcium as a white solid that is stable and non-hygroscopic. By weight, L-carnitine calcium acetate of the present invention is about 50% by weight. L-carnitine and about 12.5% by weight calcium, and L-carnitine calcium butyrate of the present invention is about 42.8% by weight. L-carnitine and about 10.7% by weight calcium. Likewise, L-carnitine calcium propionate of the present invention is about 46.2% by weight. L-carnitine and about 11.6% by weight calcium.

Dosage Forms and Therapeutic Uses of Compounds of the Present Invention. The compositions of this invention can be administered by any means that effects contact of the therapeutically active ingredients (i.e., active ingredients) with the site of action in the body of a warm-blooded animal. A most preferred administration is by the oral route (i.e., ingestion). The active ingredients can be administered by the oral route in solid dosage forms, such as tablets, capsules, powders, chewable compositions, and rapidly dissolving film, or in liquid dosage forms, such as elixirs, syrups, and suspensions. The composition is preferably made in the form of a dosage unit containing a particular amount of each active ingredient. Capsules or tablets for oral administration may contain a controlled-release formulation as may be provided in a dispersion of active compound in hydroxypropyl methylcellulose or related material known to alter the kinetics of release of the active agent. Solid dosage forms can be manufactured as sustained release products to provide for continuous release of medication over a period of hours using known pharmaceutical techniques. Compressed tablets can be sugar coated or film coated to mask any unpleasant taste and protect the tablet from the atmosphere, or enteric coated for selective disintegration in the gastrointestinal tract. Both the solid and liquid oral dosage forms can contain coloring and flavoring to increase patient acceptance.

Since an L-carnitine calcium salt of the present invention is soluble in water and aqueous solutions (such as those found in the stomach and intestine), the inventors expect that ingestion of a dosage form containing an L-carnitine calcium salt of an organic acid of the present invention by a subject will beneficially increase the plasma and red blood cell carnitine concentrations and the free/total carnitine ratios. Further, the inventors expect that subjects who ingest an L-carnitine calcium salt of an organic acid of the present invention will not experience the objectionable odor and taste that are characteristic of L-carnitine nor will they experience the acid reflux and "vinegar breath" that ensue after ingestion of calcium acetate.

A high incidence of cardiovascular disease related to abnormal lipid metabolism is very frequently found in industrialized countries. Epidemiological studies conducted over the past decade have also indicated that the development of severe coronary atherosclerosis and coronary heart disease are closely correlated with serum cholesterol levels. Treatments for abnormal lipid metabolism and coronary heart disease are designed to achieve the normalization of blood levels of triglycerides and cholesterol. Hypolipaemic drugs fall into two general categories: those which mainly reduce cholesterol and those which mainly reduce triglycerides. The former group of drugs includes the statins, probucol and cholesterol-binding resins, while the latter group includes the fibrates, nicotinic acid and niacin.

U.S. Pat. No. 3,810,994 (to Wiegand) discloses the therapeutic utility of pharmaceutical compositions of carnitine or salts, esters, or acyl derivatives thereof, for the treatment of obesity. U.S. Pat. No. 4,255,449 (Cavazza) and U.S. Pat. No. 4,268,524 (Cavazza) disclose the use of L-carnitine and alkanoyl L-carnitine to normalize the abnormal ratio between low density lipoprotein (LDL), very low density lipoprotein (VLDL), and high density lipoprotein (HDL) which is an etiological factor for various cardiovascular diseases. U.S. Pat. No. 6,180,680 (to Cavazza) discloses that the coordinated use of an alkanoyl L-carnitine and a statin is useful for treating pathologies resulting from altered lipid metabolism. U.S. Pat. No. 6,217,898 to Cavazza discloses that pharmaceutical compositions comprising L-carnitine or alkanoyl L-carnitine and hydroxycitric or pantothenic acid or derivatives thereof are useful for the prevention and treatment of disease brought about by lipid metabolism disorders. U.S. Pat. No. 6,245,800 (to Arduini, Peschechera, and Carminati) discloses a pharmaceutical composition comprising a lipid-lowering drug and L-carnitine or an alkanoyl L-carnitine, which, while conserving the efficacy of the lipid-lowering drug, is substantially devoid of the toxic or side effects typical of such lipid-lowering drugs.

The inventors have discovered that an L-carnitine calcium salt of an organic acid of the present invention may be substituted for conventional L-carnitine in compositions that are useful for preventing or treating metabolic syndromes including obesity, dyslipidemia, hypercholesterolemia, or pathologies resulting from abnormal lipid metabolism. Preferably, compositions of the present invention comprising an L-carnitine calcium salt of an organic acid of the present invention are administered substantially contemporaneously with other drug treatments or as a combination composition containing a mixture with other drug treatments. Most preferably, compositions of the present invention are administered orally.

The molecular structures of a sizeable group of registered drugs incorporate moieties comprising non-physiological, branched chain carboxylic acids having from 6 to 10 carbon atoms (including, by way of example, valproates and pivalates). Metabolism of these non-physiological, branched chain carboxylates is known to induce L-carnitine deficiency and other equally serious toxicities. The administration of conventional L-carnitine compounds is known to mitigate the adverse effects associated with receipt of drugs that incorporate moieties comprising non-physiological, branched chain carboxylic acids having from 6 to 10 carbon atoms. The inventors have discovered that an L-carnitine calcium salt of an organic acid of the present invention may be substituted for conventional L-carnitine in compositions that are useful for preventing or treating L-carnitine deficiency resulting from metabolism of non-endogenous, branched chain carboxylates having from 6 to 10 carbon atoms. Preferably, compositions of the present invention comprising an L-carnitine calcium salt of an organic acid of the present invention are administered substantially contemporaneously with other drug treatments or as a combination composition containing a mixture with other drug treatments. Most preferably, compositions of the present invention are administered orally.

A second preferred administration is by the intravenous route. The active ingredients can be administered by the intravenous route in liquid dosage forms, such as solutions, suspensions, or emulsions. The composition is preferably made in the form of a dosage unit containing a particular amount of each active ingredient.

By way of example, parenteral nutrition (PN), also known as parenteral hyperalimentation, is a medical treatment that supplies nutrition-maintaining compositions intravenously, and is indicated for a variety of mammalian disorders, such as cancer, gastrointestinal diseases, major body burns, extensive wounds, and AIDS. Partial parenteral nutrition supplies only part of daily nutritional requirements, supplementing oral intake. Many hospitalized patients receive dextrose or amino acid solutions by this method. Total parenteral nutrition treatment (TPN) supplies all daily nutritional requirements intravenously, circumventing the gut. TPN may be employed following surgery, when feeding by mouth or using the gut is not possible, when a patient's digestive system cannot absorb nutrients due to chronic disease, or, if nutrition cannot be met by enteral feeding and supplementation. Premature and sick infants often require extended periods of TPN. Compositions for parenteral nutrition generally contain at least water, glucose, amino acids, and optionally emulsified fats. They may be aseptically compounded from amino acid solutions, dextrose solutions, and/or lipid emulsions. PN compositions may further contain vitamins, electrolytes and essential trace elements. The inventors have discovered that L-carnitine calcium salts of organic acids of the present invention are compatible with PN compositions and when admixed with a PN composition provide supplemental L-carnitine, calcium, and acetate. Supplemental L-carnitine and calcium are known to improve fatty acid metabolism and bone maintenance, respectively, in humans and other warm-blooded animals.

Likewise, dialysis is a clinical treatment procedure by which metabolic by-products, toxins, and excess fluid are removed from the blood of a subject with chronic kidney disease. Dialysis may be conventionally performed as hemodialysis, in which a synthetic membrane constitutes the dialysis membrane, or as peritoneal dialysis, in which a patient's peritoneal membrane constitutes the dialysis membrane. Dialysis-related carnitine deficiency affects 95 percent of dialysis patients by six months of treatment, yet it is rarely diagnosed or treated. In 1999, the U.S. Food and Drug Administration approved L-carnitine for the prevention and treatment of carnitine deficiency in patients with end-stage renal disease who are undergoing dialysis. FDA approval was based, in part, on a compelling body of data from many studies that have confirmed that correcting carnitine deficiency can lead to improved response to erythropoietin, decreased intradialytic hypotension, decreased metabolic dysfunction, improved quality of life, and a significant decrease in hospitalizations of subjects with chronic kidney disease. Since intradialytic hypotension is associated with significant morbidity, long-term L-carnitine therapy may also increase the life span of renal disease patients. The inventors have discovered that an L-carnitine calcium salt of an organic acid of the present invention may be formulated for intravenous administration to a subject with chronic kidney disease and expect that intravenous administration of a formulation of an L-carnitine calcium salt of an organic acid will address an unmet need for provision of L-carnitine by providing L-carnitine as an L-carnitine calcium salt of the present invention in sufficient quantity to correct carnitine deficiency and improve response to erythropoietin, decrease intradialytic hypotension, decrease metabolic dysfunction, improve quality of life, and significantly decrease the number and duration of hospitalizations of subjects with chronic kidney disease.

In general, the pharmaceutical compositions of this invention can be prepared by conventional techniques, as are described in *Remington's Pharmaceutical Sciences*, a standard reference in this field [Gennaro A R, Ed. *Remington: The Science and Practice of Pharmacy.* 20$^{th}$ Edition. Baltimore: Lippincott, Williams & Williams, 2000]. For therapeutic purposes, the active components of this invention are ordinarily combined with one or more excipients appropriate to the indicated route of administration.

The following examples present useful compositions of the present invention and their anticipated outcomes in treating calcium and/or L-carnitine deficits in subjects requiring such treatment. The examples are representative of the scope of the invention, and as such are not to be considered or construed as limiting the invention recited in the appended claims.

EXAMPLE 1

Attempted preparation of L-carnitine calcium tartrate. A mixture of tartaric acid (0.46 g, 0.003 mol), calcium hydroxide (0.22 g, 0.003 mol) and L-carnitine (0.5 g, 0.003 mol) was dissolved in water (15 mL) and stirred for 1 hour. Incomplete dissolution was observed and stirring was continued overnight. The temperature was raised to 70° C. and maintained for four hours. Dissolution remained incomplete. The reaction mixture was cooled to room temperature and filtered. The filtrate was concentrated at reduced pressure to a white solid. The solid had a distasteful "fishy" odor that was similar to that of L-carnitine.

EXAMPLE 2

Attempted preparation of L-carnitine calcium succinate. A mixture of calcium succinate (0.85 g, 0.003 mol) and L-carnitine (0.5 g, 0.003 mol) was dissolved in water (5 mL) and stirred at room temperature for 30 minutes. Dissolution was incomplete, and the reaction temperature was raised to 80° C. Stirring was continued at the higher temperature for 3 hr. The resulting solution was cooled to room temperature and filtered, and the filtrate was concentrated at reduced pressure to a white solid. On exposure to the atmosphere, the solid absorbed water and became "sticky." In other words, L-carnitine calcium succinate was found to be hygroscopic.

EXAMPLE 3

Attempted preparation of L-carnitine calcium salt. A mixture of calcium hydroxide (0.22 g, 0.003 mol) was suspended in acetone (100 mL) and a concentrated solution of L-carnitine (0.5 g, 0.003 mol) in the minimum volume of water needed to effect dissolution was added. The resulting reaction mixture was heated at reflux for 4 hours. Dissolution remained incomplete. The reaction mixture was filtered hot. The filtrate was concentrated at reduced pressure to a white solid. On exposure to the atmosphere, the solid absorbed water and became "sticky." In other words, L-carnitine calcium salt was found to be hygroscopic.

EXAMPLE 4

Attempted preparation of L-carnitine calcium fumarate. A mixture of fumaric acid (0.35 g, 0.003 mol), calcium hydroxide (0.22 g, 0.003 mol) and L-carnitine (0.5 g, 0.003 mol) was dissolved in water (5 mL) and stirred and heated at 80° C. for 2 hours. The reaction mixture was concentrated to a white solid. The solid had a distasteful "fishy" odor that was similar to that of L-carnitine and was found to be hygroscopic.

EXAMPLE 5

Preparation of L-carnitine calcium acetate. A mixture of calcium acetate (0.5 g, 0.003 mol) and L-carnitine (0.5 g, 0.003 mol) was dissolved in water (15 mL) and stirred for 2 hours. The clear and colorless solution was concentrated at reduced pressure at bath temperatures that were less than about 70° C. to a white solid. The solid, L-carnitine calcium acetate, was obtained in greater than 90% yield and had a melting point of 166-167° C., with decomposition and evolution of trimethylamine. (The melting point of L-carnitine was 186-190° C.) The solid was not hygroscopic. The solid had no objectionable taste. The $^1$H-Nuclear Magnetic Resonance ($^1$H-NMR) spectrum (FIG. 1) is consistent with the structure of the salt and shows the presence of L-carnitine and acetate in a molar ratio of approximately 1:2. (Calcium is not detected by $^1$H-NMR.)

EXAMPLE 6

Preparation of L-Carnitine calcium butyrate. L-Carnitine (0.5 g, 0.003 mol) and butyric acid (0.54 g, 0.006 mol) were added to 5 mL of water and 1 mL of methanol. To the resulting solution was added calcium hydroxide (0.22 g, 0.003 mol). The resulting slurry clarified during 15 minutes of stirring at room temperature. After continued stirring at room temperature for four hr, the solution was filtered, and the filtrate was concentrated to dryness under vacuum at bath temperatures that were less than about 70° C. The solid, L-carnitine calcium butyrate, was obtained in greater than 90% yield and had a melting point of 97.6° C., with decomposition and evolution of trimethylamine. (The melting point of L-carnitine was 186-190° C. Butyric acid is a liquid.) The solid was not hygroscopic. The solid had no objectionable taste but had a somewhat bitter aftertaste. The $^1$H-NMR spectrum (FIG. 2) is consistent with the structure of the salt and shows the presence of L-carnitine and butyrate in a molar ratio of approximately 1:2. (Calcium is not detected by $^1$H-NMR.)

EXAMPLE 7

Preparation of L-carnitine calcium propionate. L-Carnitine calcium propionate was prepared by combining L-carnitine (0.5 g. 0.003 mol) and calcium propionate (0.55 g, 0.003 mol) in about 4 mL of water. When dissolution was complete, the clear and colorless solution that results was stirred for about 15 minutes and then concentrated to dryness under vacuum, using a water bath that was maintained at less than about 70° C. L-Carnitine calcium propionate, a white solid that is not hygroscopic, was obtained in greater than 90% yield. L-Carnitine calcium propionate has a melting point of about 166.3° C. (with decomposition and evolution of trimethylamine). The $^1$H-NMR spectrum (FIG. 3) is consistent with the structure of the salt and shows the presence of L-carnitine and propionate in a molar ratio of approximately 1:2. (Calcium is not detected by $^1$H-NMR.) The solid has a very slight odor and no objectionable taste.

EXAMPLE 8

Determination of hygroscopicity or deliquescence of L-carnitine compounds. The hygroscopicity or deliquescence of L-carnitine compounds was determined in the following manner. An accurately weighed portion of each compound was weighed into a separate, tared glass container that was open to the ambient atmosphere. Periodically during the storage period that followed, each sample was re-weighed and the mass recorded. At the end of the 6-day storage period, the change in mass at each interval was determined (Table 2). A 1% or greater increase in mass indicates that the compound is hygroscopic (absorbs water). A 1% or greater decrease in mass indicates that the compound is deliquescent. A change in mass of less than 1% indicates that the compound is stable and non-hygroscopic. The data showed that L-carnitine calcium acetate did not absorb water and was stable during storage. Laboratory observations indicated that L-carnitine calcium butyrate and L-carnitine calcium propionate exhibit lack of hygroscopicity or deliquescence as well.

TABLE 2

Data from exposure study

| Material | Net weight, initial | Net weight, final | Conclusion & Observations |
|---|---|---|---|
| L-Carnitine (Sigma Aldrich Chemical Co.) | 208.1 mg | >226.8 mg (+>8%) | The sample absorbed water from the atmosphere and the weight increased. The material adhered to the glass vessel and gradually dissolved in the absorbed water. Material is hygroscopic. |
| L-Carnitine calcium acetate | 149.0 mg | 149.5 mg (+0.3%) | Appearance and mobility of the material did not change. Material did not absorb water and was stable during storage. |
| L-Carnitine calcium propionate | 161.8 mg | 170.2 mg (+5%) | When the relative humidity was less than about 20%, the appearance and mobility of the material did not change. At higher relative humidities, mobility of the material changed as the material absorbed water. Compound became "sticky." |

The following examples present hypothetically useful applications of representative compositions of the present invention and their anticipated outcomes in treating subjects at risk for or having L-carnitine or calcium deficiency. The examples are representative of the scope of the invention, and as such are not to be considered or construed as limiting the invention recited in the appended claims.

EXAMPLE 9

Physiological effects of administration by injection of a solution of L-carnitine. The following study, which was reported by Golper et al., shows that conventional L-carnitine, administered intravenously, increased plasma and red blood cell total carnitine concentrations eightfold. [Golper T A, Wolfson M, Ahmad S, Hirschberg R, Kurtin P, Katz L A, Nicora R, Ashbrook D, Kopple J D. Multicenter trial of L-carnitine in maintenance hemodialysis patients. I. Carnitine concentrations and lipid effects. Kidney Int 1990; 38: 904-911.]

Study design and populations. The study followed a double-blinded, parallel group, placebo control design. All patients selected to participate were randomized separately at each study center into treatment or control groups using a modified 4×4 Latin square. Patients were stratified by sex. Individuals first entered into a one-month baseline period. From the termination of the baseline period through the next six months, either placebo or L-carnitine was administered. The drug or placebo was injected over one to three minutes in the venous line during the blood return immediately after the end of every dialysis treatment. All subjects were dialyzed thrice weekly except for two placebo recipients who were dialyzed twice weekly.

The L-carnitine preparation was a 20% solution in water (VitaCarn®, Kendall McGaw Laboratories, Inc., Irvine, Calif., USA). The placebo consisted of 0.9% sodium chloride injection, USP. Each subject received 0.1 ml of solution per kg of edema-free body weight. For the subjects receiving L-carnitine, this provided 20 mg of compound per kg.

Inclusion criteria were as follows: stable maintenance hemodialysis patients of either sex over 18 years of age, written informed consent, permission by the primary care physician, a duration of hemodialysis therapy of at least nine months, a prognosis to survive for the duration of the study, the potential to comply with and complete the study, and no imminent prospect of renal transplantation. Clinically stable patients were defined as those who were generally compliant with their dietary, fluid and dialytic regimens.

Exclusion criteria were as follows: medical instability (see paragraph above and in addition this excluded patients who had frequent and/or repeated hospital admissions), previous unreliable behavior patterns, diabetes mellitus with fasting serum glucose≧140 mg/dL or treated with oral hypoglycemic agents or insulin endocrinopathies known to interfere with lipid metabolism, known genetic defects in lipid metabolism, previous or current carnitine therapy, lipid lowering drug therapy, class IV angina, liver failure, malignant hypertension, a high likelihood of an imminent living donor transplantation, and the presence of malignancies other than basal cell carcinomas of the skin. Patients were not excluded if they were receiving drugs that have been associated with elevating plasma lipids, in particular beta-adrenergic blocking agents and androgens. The protocol stipulated that patients could be removed from the study for significant metabolic or technical complications, for clinically significant adverse reactions, or at their request or that of their primary care physician.

All patients gave informed written consent to participate in this investigation. Approval was obtained from each participating center's internal review board.

Methods. Each participating center sent its blood samples to the same laboratory for analysis of carnitine. Other special studies, such as creatine kinase, were also performed in one laboratory. For the hemograms and serum biochemistries all measurements in all patients were performed in the same clinical laboratory. Twice during the baseline period and monthly during the treatment phase fasting whole blood samples were inflected in EDTA immediately before dialysis for determination of plasma and red cell total carnitine and plasma lipids. Post-dialysis samples were also collected for plasma and RBC carnitine. Plasma and packed red cells were separated by centrifugation and stored at −70° C. until analyzed.

Open vastus lateralis muscle biopsies were performed under local anesthesia during baseline and month six of treatment. The tissue was frozen in liquid nitrogen and stored at −70° C. until shipped. Muscle carnitine determinations were performed using a modification of the technique of Cederblad and Lindstedt.

Statistical analysis. Clinical data were tabulated by descriptive statistics (mean±SEM). Statistical analyses within and between treatment groups were performed using paired and unpaired t-tests and general univariate and multivariate analysis of variance with repeated measures (weighted ANOVA system).

EXAMPLE 10

Physiological effects of administration by injection of a solution of L-carnitine calcium acetate. The inventors expect that a study paralleling that of Golper et al. (Example 9, vide infra) may be completed in which L-carnitine calcium acetate of the present invention is substituted for the L-carnitine of Golper et al. L-Carnitine calcium acetate of the present invention has a known molecular weight and composition and is water soluble. Therefore, intravenously administrable solutions of L-carnitine calcium acetate can be prepared that will provide a known concentration of L-carnitine. The intravenously administrable solutions of L-carnitine calcium acetate of the present invention may be provided to test subjects as sterile aqueous solutions of L-carnitine calcium acetate which will be administered by injecting over one to three minutes in the venous line during the blood return immediately after the end of every dialysis treatment. In the alternative, the inventors expect that the unique physico-chemical properties of L-carnitine calcium acetate of the present invention will permit incorporation of L-carnitine calcium acetate into dialysate as a source of L-carnitine and as a partial or total replacement for the calcium that is conventionally included in dialysate. If L-carnitine calcium acetate is provided as an intravenous injection, either in the venous line during blood return or in dialysate, the inventors expect that the clinical benefit of this intravenous administration will be shown by measurable increases in plasma and red blood cell carnitine concentrations and in the total/free carnitine ratio that are similar to the increases observed by Golper et al. after administration of L-carnitine.

EXAMPLE 11

Physiological effects of ingestion of an L-carnitine calcium acetate medical food preparation. Soft-gel capsules containing a mixture of L-carnitine calcium acetate (500 mg per capsule; test article) and inactive excipients are prepared. After testing to determine their plasma and red blood cell L-carnitine concentration and total/free carnitine ratios, ten adults will ingest a single test article a day for a period of 180 days. Twice during the baseline period and monthly during the treatment phase, fasting whole blood samples will be collected in EDTA for determination of plasma and red cell total carnitine. Plasma and packed red cells will be separated by centrifugation and stored at −70° C. until analyzed. Free and acyl carnitine determinations will be performed at baseline and after three and six months of treatment. Clinical data will be tabulated by descriptive statistics (mean±SEM). Statistical analyses within and between treatment groups will be performed using paired and unpaired t-tests and general univariate and multivariate analysis of variance with repeated measures (weighted ANOVA system). Since an L-carnitine calcium salt of the present invention is soluble in water and aqueous solutions (such as those found in the stomach and intestine), the inventors expect that ingestion of an L-carnitine calcium salt of an organic acid of the present invention by a subject will beneficially increase the plasma and red blood cell carnitine concentrations and the free/total carnitine ratios. Further, the inventors expect that subjects who ingest an L-carnitine calcium salt of an organic acid of the present invention will not experience the objectionable odor and taste that are characteristic of L-carnitine nor will they experience the acid reflux and "vinegar breath" that ensue after ingestion of calcium acetate.

All references discussed herein are incorporated by reference. One skilled in the art will readily appreciate that the present invention is well adapted to carry out the objects and obtain the ends and advantages mentioned, as well as those inherent therein. The present invention may be embodied in other specific forms without departing from the spirit or essential attributes thereof and, accordingly, reference should be made to the appended claims, rather than to the foregoing specification, as indicating the scope of the invention.

We claim:

1. A stable, non-hygroscopic L-carnitine salt composition having the formula:

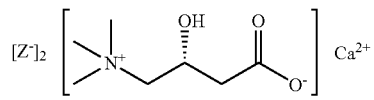

wherein Z is acetate, propionate, or butyrate.

2. A method for preparing an L-carnitine calcium salt composition having the formula:

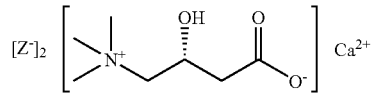

wherein Z is an anion of an organic acid selected from the group consisting of acetate, propionate, and butyrate, comprising reacting L-carnitine, calcium ion, and the anion of an organic acid in a 1:1:2 molar ratio in a suitable solvent and obtaining the product of said reaction.

3. A method for preventing the onset or reversing the course of deleterious effects brought about by L-carnitine or calcium deficiency comprising administering an L-carnitine salt composition having the formula:

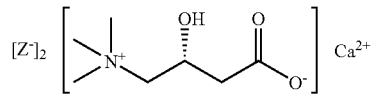

wherein Z is acetate, propionate, or butyrate in a dose sufficient to restore the L-carnitine or calcium concentration to normal physiological levels in a subject.

4. The method of claim 3 wherein the method of administering is oral, intravenous, or parenteral.

5. The method of claim 3 wherein the method of administering provides a therapeutically effective amount of the L-carnitine calcium composition.

6. The method of claim 3, further comprising administering the L-carnitine calcium composition for treating a disease selected from the group consisting of osteoporosis, metabolic syndrome, obesity, chronic kidney disease, malnutrition, inflammatory bowel disease, and malnutrition that is treated by infusion of parenteral hyperalimentation solutions.

* * * * *